United States Patent
Wu et al.

(10) Patent No.: US 8,349,582 B2
(45) Date of Patent: Jan. 8, 2013

(54) HIGH-EFFICIENCY VIABLE SAMPLER FOR ULTRAFINE BIOAEROSOLS

(75) Inventors: Chang-Yu Wu, Gainesville, FL (US); Alexandros Demetrios Theodore, Plantation, FL (US); Jin-Hwa Lee, Plano, TX (US); Lindsey Ann Riemenschneider, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 342 days.

(21) Appl. No.: 12/673,753

(22) PCT Filed: Aug. 15, 2008

(86) PCT No.: PCT/US2008/073267
§ 371 (c)(1),
(2), (4) Date: Feb. 16, 2010

(87) PCT Pub. No.: WO2009/026130
PCT Pub. Date: Feb. 26, 2009

(65) Prior Publication Data
US 2011/0111387 A1 May 12, 2011

Related U.S. Application Data

(60) Provisional application No. 60/956,316, filed on Aug. 16, 2007.

(51) Int. Cl.
*C12Q 1/70* (2006.01)
*C12Q 1/68* (2006.01)
*C12Q 1/02* (2006.01)
*C12Q 1/24* (2006.01)
*C12N 7/02* (2006.01)
*C12M 1/00* (2006.01)
*C12M 3/00* (2006.01)

(52) U.S. Cl. .............. 435/30; 435/5; 435/6.15; 435/29; 435/31; 435/309.1; 435/283.1; 435/287.1; 435/288.1

(58) Field of Classification Search ................. None
See application file for complete search history.

(56) References Cited

U.S. PATENT DOCUMENTS

| | | | | |
|---|---|---|---|---|
| 2,825,872 | A * | 3/1958 | Stubbs et al. | 324/71.1 |
| 4,899,551 | A * | 2/1990 | Weintraub | 62/176.6 |
| 5,855,652 | A | 1/1999 | Talley | |
| 6,958,234 | B2 | 10/2005 | Aicher | |
| 6,993,985 | B2 | 2/2006 | Srebro | |
| 7,125,437 | B2 | 10/2006 | Bryden et al. | |
| 7,201,878 | B2 | 4/2007 | Lin et al. | |
| 7,767,150 | B1 * | 8/2010 | Zaromb et al. | 422/400 |

OTHER PUBLICATIONS

Zhou et al. Medical Nebulizer Performance: Effects of Cascade Impactor Temperature. Respiratory Care 2005, vol. 50, No. 8, pp. 1077-1082.*
Holdren et al. Development and Evaluation of a Thermoelectric Cold Trap for the Gas Chromatographic Analysis of Atmospheric Compounds. Analytical Chemistry 1998, vol. 70, No. 22, pp. 4836-4840.*
Sattar et al. Effect of relative humidifty on the airborne survival of rotavirus SA11. Applied Environmental Microbiology 1984, vol. 47, No. 4, pp. 879-881.*

* cited by examiner

*Primary Examiner* — Louise Humphrey
(74) *Attorney, Agent, or Firm* — MH2 Technology Law Group, LLP

(57) ABSTRACT

Exemplary embodiments provide bioaerosol detection systems and methods for detecting bioaerosols. In one embodiment, the bioaerosol detection system can include a humidifier to increase the humidity of a continuously flowing sample volume of a bioaerosol sample using a biologically compatible liquid medium, and an amplifier to deposit vapor on the bioaerosol sample for a particle size amplification process. Bioaerosol(s) can thus be detected and sampled while simultaneously maintaining their viability. The disclosed bioaerosol detection systems and the methods can provide high efficiency for sampling and detecting ultrafine bioaerosol(s) such as viruses and proteins, which can be smaller than 0.3 μm in diameter and can be as small as 20 nm.

20 Claims, 5 Drawing Sheets

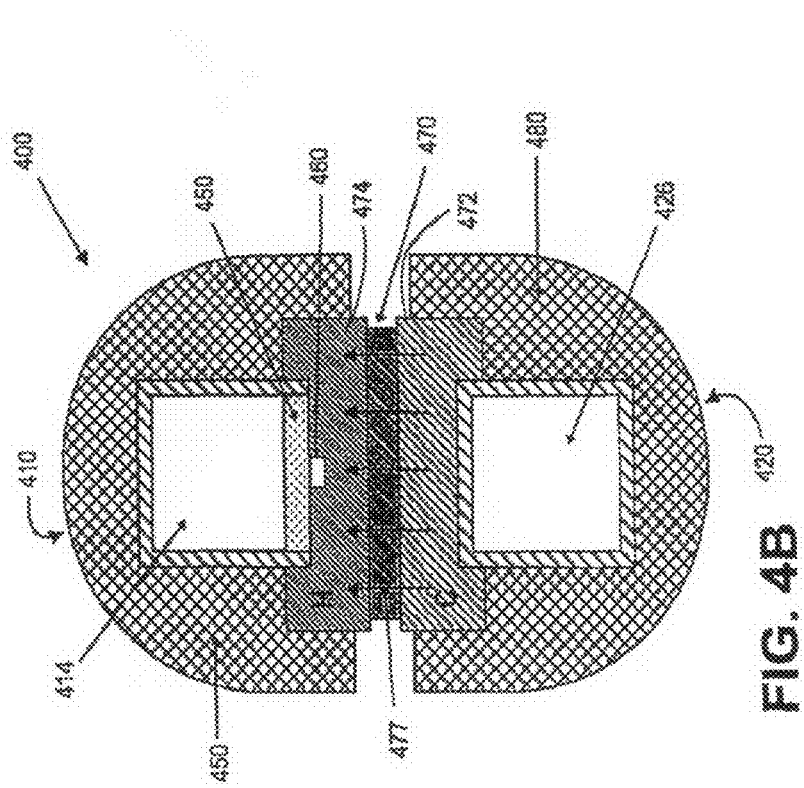
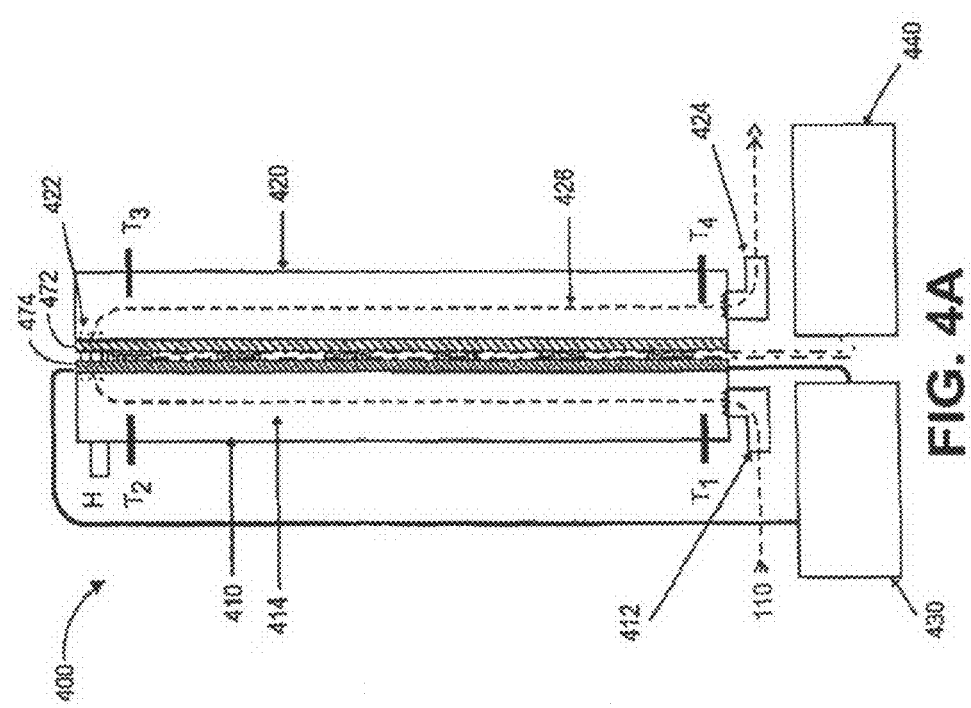
FIG. 4B
FIG. 4A

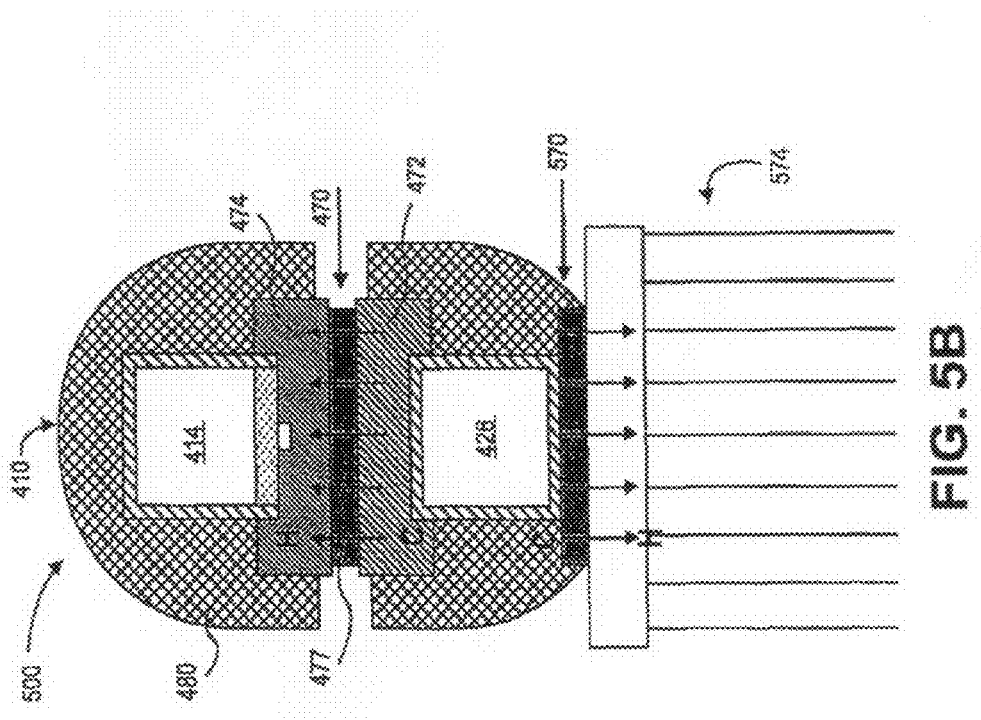
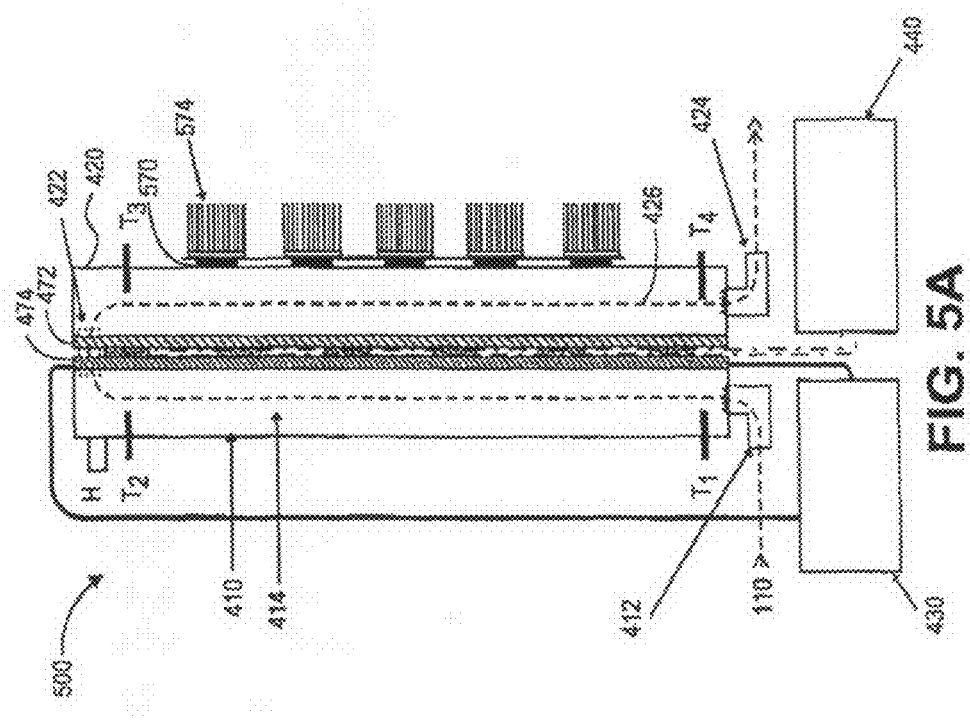

HIGH-EFFICIENCY VIABLE SAMPLER FOR ULTRAFINE BIOAEROSOLS

RELATED APPLICATIONS

This application claims priority to U.S. Provisional Patent Application No. 60/956,316, filed Aug. 16, 2007, and is a national phase application of PCT/US20081073267 filed on Aug. 15, 2008, the disclosure of which is incorporated by reference herein in its entirety.

GOVERNMENT RIGHTS

This invention was made with government support under Contract No. FA8650-606-CO5913 awarded by the United States Air Force (USAF). The government has certain rights in the invention.

FIELD OF THE INVENTION

This invention relates generally to bioaerosols and, more particularly, to a system for detecting bioaerosols.

BACKGROUND OF THE INVENTION

Bioaerosols typically occur in very low concentrations making them very hard to detect. Bioaerosols can be found in the workplace, in residences, in medical facilities, in manufacturing operations, in animal processing facilities, in dairy facilities or other animal houses, in recycling or composting plants, in sanitary landfills, in sewage plants, etc. Airborne microorganisms or bioaerosols can cause disease, allergies, and respiratory problems. Bioaerosols are increasingly feared as being potential bio-warfare and terrorist agents.

There are many aerosol detection and sampling systems. However, most of them are for inert aerosols and their designs do not consider the viability of bioaerosols. Furthermore, they are not capable of distinguishing biological agents from inert agents in the same sample volume.

A known method of detecting and identifying bioaerosols is disclosed in U.S. Pat. No. 6,806,464. An aerosol time-of-flight mass spectrometer using fluorescence techniques is used to ionize selected bioaerosol particles. Laser radiation using a wavelength which is specific to substances affects fluorescence. A fluorescence detector is used to select the bioaerosol particles, and a second laser is used to emit light of a wavelength that effects the ionization of the bioaerosol particles selected by the fluorescence detector. Such a method of detecting and identifying a bioaerosol is rather complex, relying on relatively expensive and complex equipment. Furthermore, the method has not been demonstrated to be able to accurately identify speciation and quantify viable concentration in practical applications.

Other methods for bioaerosol detection rely on impaction or impingement. This is accomplished using inertial forces either by impaction on plates, such as that used in an Anderson Impactor, loaded with agar or by impingement into a liquid, such as that used in an All Glass Impinger or a Bio-Sampler (U.S. Pat. No. 5,902,385). Because inertia is a function of particle size, particle size plays a critical role in determining the ability to sample and quantify bioaerosols; in general, the larger the size, the higher the collection efficiency.

An impactor is a device with nozzles that direct air flow carrying aerosol toward impaction plates. The inertia of the aerosol drives its impaction, and therefore its collection efficiency decreases as aerosol size decreases. The collection efficiency can be increased by applying low pressure or by applying a higher velocity. Unfortunately, this approach dries out agar quickly and therefore cannot be used for collecting viable bioaerosols. Existing viable impactors such as the Anderson Impactor can only collect down to 0.6 µm due to this limitation.

An impinger is a container with nozzles and an aqueous collection medium. Air flow exiting the inlet nozzle(s) form bubbles in the liquid. Aerosol in the bubbles can leave the bubbles due to its inertia, and therefore the collection efficiency decreases as its size decreases. Available impingers such as All Glass Impingers have less than 70% efficiency for particles less than 0.5 µm. The BioSampler, which is an improved version using swirling jets, still has only 80% efficiency for 0.3 µm. As described, either a viable impactor or an impinger has low efficiency for bioaerosols below 0.3 µm. According to Hogan et al. ("Sampling Methodologies and Dosage Assessment Techniques for Submicrometer and Ultrafine Virus Aerosol Particles", Applied Microbiology, 99, p. 1422-1434, 2005), the efficiency of BioSamplers and All Glass Impingers for collecting MS2 bacteriophage is less than 10%.

Thus, there is a need to overcome these and other problems of the prior art and to provide a high-efficiency viable detecting system for ultrafine bioaerosols.

SUMMARY OF THE INVENTION

According to various embodiments, the present teachings include a bioaerosol detection system. Specifically, the bioaerosol detection system can include a humidifier and an amplifier. The humidifier can bind a biocompatible liquid with one or more bioaerosols of a continuously flowing sample volume; while the amplifier can allow a size amplification of the one or more bioaerosols of the continuously flowing sample volume from the humidifier.

According to various embodiments, the present teachings also include a method of detecting a bioaerosol. In this method, the humidity of a continuously flowing sample volume containing one or more bioaerosols can be first increased, followed by an effective amplification of the humidified one or more bioaerosols by condensing vapor thereon.

According to various embodiments, the present teachings further include a bioaerosol detection system. The bioaerosol detection system can include (1) a humidifier to bind a biocompatible liquid with one or more bioaerosols of a continuously flowing sample volume; (2) a nebulizer device connected to the humidifier to further control a humidity of the one or more bioaerosols; (3) an amplifier to allow size amplification of the humidified one or more bioaerosols; (4) a plurality of heat pumps disposed between the humidifier and the amplifier to provide a temperature difference between the humidifier and the amplifier; (5) a secondary set of heat pumps connected to the amplifier to further control the temperature difference between the humidifier and the amplifier; and/or (6) one or more of a biocompatible impinger, a biocompatible impactor, a biocompatible cyclone separator and a biocompatible electrostatic precipitator to collect the amplified bioaerosols.

Additional objects and advantages of the invention will be set forth in part in the description which follows, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 4A-4B show an exemplary condensational amplification system for FIG. 1 in accordance with the present teachings.

FIGS. 5A-5B show another exemplary condensational amplification system for FIG. 1 in accordance with the present teachings.

DESCRIPTION OF THE EMBODIMENTS

Figure 1:
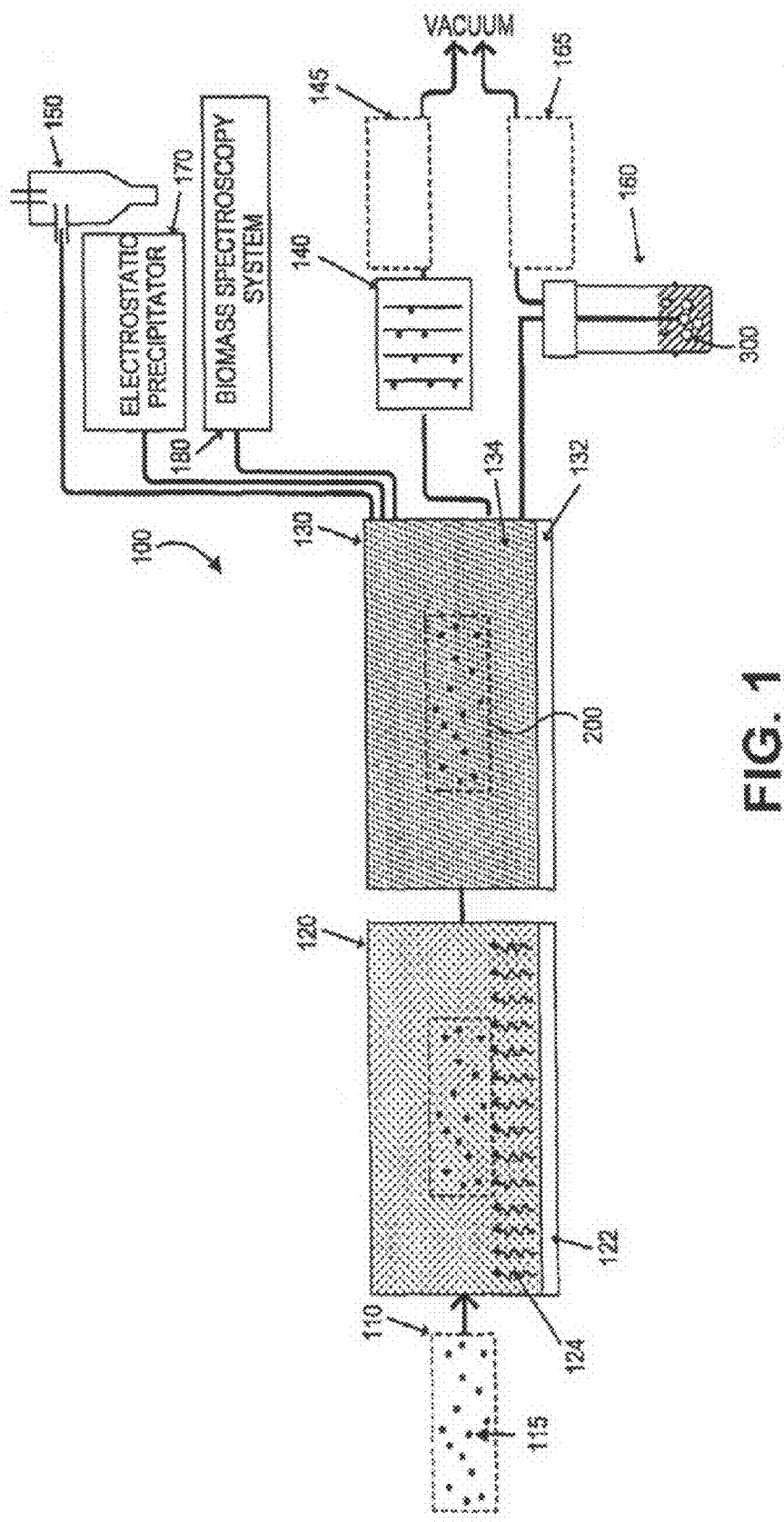
FIG. 1 shows an exemplary bioaerosol detection system in accordance with the present teachings.

Reference will now be made in detail to the present embodiments (exemplary embodiments) of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Exemplary embodiments provide bioaerosol detection systems and methods for detecting bioaerosols. In one embodiment, the bioaerosol detection system can include a humidifier to increase the humidity of a continuously flowing sample volume of a bioaerosol sample using a biologically compatible liquid medium, and an amplifier to deposit vapor on the bioaerosol sample for a particle size amplification process. Bioaerosol(s) can thus be detected and sampled while simultaneously maintaining their viability. The disclosed bioaerosol detection systems and the methods can provide high efficiency for sampling and detecting ultrafine bioaerosol(s) such as viruses, which can be smaller than 0.3 μm in diameter and can be as small as 20 nm.

FIG. 1 shows an exemplary bioaerosol detection system 100 in accordance with the present teachings. It should be readily apparent to those of ordinary skill in the art that the bioaerosol detection system 100 shown in FIG. 1 represents a generalized system illustration and that other components can be added or existing components can be removed or modified while still remaining within the spirit and scope of the present teachings.

In particular, the bioaerosol detection system 100 can include a humidifier (or saturator) 120, and a particle amplifier 130. The bioaerosol system 100 can also include an impactor 140 connecting to a first vacuum 145, a cyclone separator 150, an impinger 160 connecting to a second vacuum 165, an electrostatic precipitator 170, and/or a biomass spectroscopy system 180. For illustrative purpose, FIG. 1 only shows the impactor 140 and the impinger 160 being adaptively connected to the vacuum. Various embodiments can include that the cyclone separator 150, the electrostatic precipitator 170, and/or the biomass spectroscopy system 180 can also include a vacuum adaptively attached thereto.

As shown in FIG. 1, a sample volume 110 can contain one or more bioaerosols 115 having a dimensional scale on the order of submicron or nanometer. For example, the bioaerosol(s) 115 can be about 10 nm to about 300 nm in diameter. Specifically, the bioaerosol(s) can include, e.g., MS2 coli phage having a diameter of about ~28 nm; Variola (Smallpox) virus having a diameter of about ~250 nm; Human corona virus having a diameter of about 60 nm to about 120 nm; Hanta virus having a diameter of about 100 nm to about 270 nm; and Venezuelan equine encephalitis virus (VEEV) having a diameter of about 60 nm.

The bioaerosol(s) 115 can be drawn into the humidifier/saturator 120 through vacuum action produced by the first vacuum 145 and/or the second vacuum 165. The humidifier/saturator 120 can include a heating source 122 that creates a humid environment by evaporating a liquid source 124 to higher than room temperature, e.g. about 35° C., but not too high to deactivate the biological agents, e.g., less than about 45° C. The liquid source 124 can contain any of a number of easily evaporated liquids that is biologically compatible, e.g., water. The evaporation of the liquid source 124 can produce a relative humidity ("RH") within the humidifier/saturator 120 of about 90% or higher. In various embodiments, the duration of the sample volume 110 that is subjected to the RH within the humidifier/saturator 120 can be as lithe as the time that it takes the sample volume 110 to pass through the humidifier/saturator 120, e.g., about 1 second or less.

The sample volume 110 can then be drawn into the amplifier 130 through vacuum action produced by the first vacuum 145 and/or the second vacuum 165. The amplifier 130 can include a cooling source 132 that lowers the amplifier temperature to less than the ambient, e.g. about 10° C. The sample volume 110 within the amplifier 130 can be subjected to condensation with the supersaturated vapor 134, where the bioaerosol serves as the condensation nuclei from which a particle grows, e.g., as shown in FIG. 2, while maintaining the viability of the biological agent.

Figure 2:
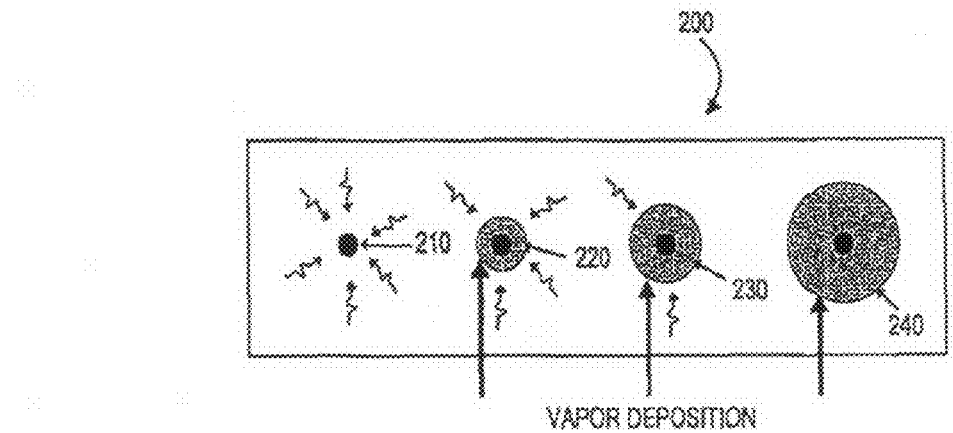
FIG. 2 is a schematic for an exemplary bioaerosol particle size amplification of FIG. 1 in accordance with the present teachings.

FIG. 2 is a schematic for the particle size amplification 200 based on the bioaerosol condensation nuclei of a sample volume in accordance with the present teachings. It should be readily apparent to those of ordinary skill in the art that the particle size amplification 200 shown in FIG. 2 represents a generalized system illustration and that other components can be added or existing components can be removed or modified while still remaining within the spirit and scope of the present teachings.

The result of the particle size amplification 200 of a sample volume can be shown from an ultrafine particle 210, such as the bioaerosol condensation nuclei to a supermicron droplet 240 containing the bioaerosol condensation nuclei. The result of the particle size amplification of the bioaerosols can be used to improve the detection and sampling of the bioaerosols. Note that although particle size amplification 200 is shown in FIG. 2 to include four stages, one of ordinary skill in the art will understand that particle size amplification 200 can occur incrementally without defined stages.

In various embodiments, the condensation of the supersaturated vapor 134 can result in particle size amplification of the bioaerosols from a scale on the order of nanometer and/or submicron to a much greater size. For example, the amplified bioaerosols can have a size of, e.g., about 0.3 μm or higher. In an additional example, the condensation within the amplifier 130 can amplify the bioaerosols into a great size of about 10 μm or higher. Note that a particle of about 10 μm is much more favorable than a particle of about 0.1 μm for its collection by impaction or impingement. Meanwhile, the supersaturated vapor 134 can provide biological compatibility (i.e., biocompatibility) and can serve as a protective means to maintain the viability of the biological agents of the bioaerosols (see 210, 220, 230 and/or 240 in FIG. 2) in the sample volume 110 from environmental factors (e.g. desiccation).

Referring back to FIG. 1, the duration during which the sample volume 110 can have condensational amplification of bioaerosol(s) within the amplifier 130 with the supersaturated vapor 134 can be as little as the time that it takes the sample volume 110 to pass through the amplifier 130, e.g., about 1 second or less.

In this manner, the sample volume 110 with bioaerosol(s) can first be drawn through the humidifier or saturator 120 allowing the binding of the bioaerosol(s) to a biocompatible liquid and then through the amplifier 130 allowing for particle size amplification of bioaerosol(s) to increase their dimensions/concentrations and increase detection efficiency. In various embodiments, the combination of the humidifier 120 and the amplifier 130 can form a particle size amplification system.

The amplified bioaerosol(s) exiting amplifier 130 can also be fed directly into the biomass spectroscopy system 180 for in-line and continuous identification. Exemplary biomass spectroscopy systems can include those described in Journal of Aerosol Science, entitled "Matrix-Assisted Laser Desorption/Ionisation Aerosol Time-of-Flight Mass Spectrometry for the Analysis of Bioaerosols: Development of a Fast Detector for Airborne Biological Pathogens," the entirety of which is incorporated by reference herein. In various embodiments, the disclosed biomass spectroscopy system 180 can detect amplified bio-species/bioaerosols from a small size, e.g., detect viruses, which can not be detected when using a conventional system in the prior art. In various embodiments, other bioaerosol(s) including, but not limited to, bacteria and protein can be amplified, detected or sampled by the biomass spectroscopy system 180. In various embodiments, the biomass spectroscopy system 180 can include a vacuum adaptively attached thereto.

In one example, the sample volume 110 with amplified bioaerosol(s) within the amplifier 130 can be pulled into the impactor 140, e.g., a multi-stage or a single-stage viable/biocompatible impactor, by the first vacuum 145. The bioaerosol(s) can then be removed from the sample volume 110 by the impactor 140. That is, the bioaerosol(s) can be collected by the impactor 140 and the sample volume 110 leaving the first vacuum 145 can no longer contain the bioaerosol(s).

Figure 3:
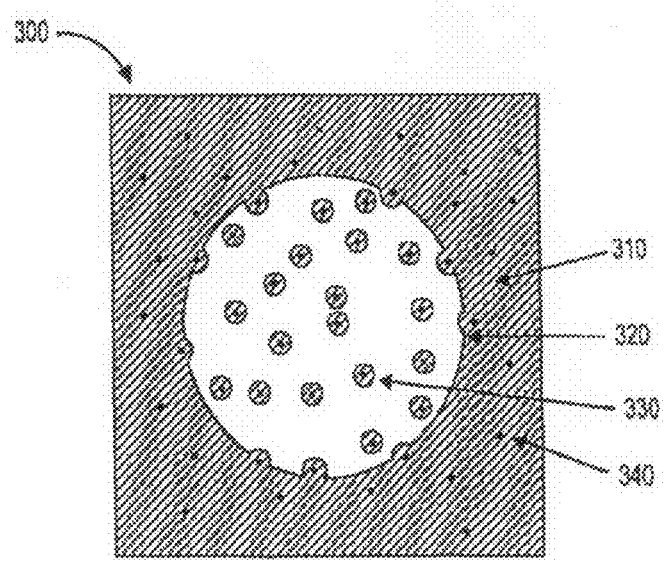
FIG. 3 shows an exemplary bubble sample in an impinger fluid of FIG. 1 in accordance with the present teachings.

In another example, the sample volume 110 with amplified bioaerosol(s) within amplifier 130 can be pulled into the impinger 160 by the second vacuum 165. The sample volume 110 can form bubbles of amplified bioaerosol(s) within the impinger 160, which is shown in FIG. 3. For example, after leaving the amplifier 130, the sample volume 110 can be drawn through an immersion fluid in the impinger 160 by the second vacuum 165 and thereby form bubbles within the immersion fluid. The amplified bioaerosol(s) can then be removed from the sample volume 110 by the impinger 160. That is, the bioaerosol(s) can be collected by the impinger 160 and the sample volume 110 leaving the first vacuum 165 can no longer contain the bioaerosol(s).

In an additional example, the sample volume 110 with grown bioaerosols within amplifier 130 can be pulled into the cyclone separator 150. The cyclone separator 150 can be biocompatible and can be operated based on inertia collection. Unlike the impactor that relies on perpendicular impaction, the cyclone separator 150 can use the centrifugal force in a curved path to separate the aerosol particles from the gas stream, i.e., the continuously flowing sample volume 110. The liquid aerosol that hits the cyclone surface can then be drained down and can be collected in a reservoir below (not illustrated).

In a further example, the sample volume 110 with grown bioaerosols within amplifier 130 can be pulled into the electrostatic precipitator 170. The electrostatic precipitator 170 can be biocompatible and can rely on electrostatic attraction for collecting aerosol(s). For example, charges produced by an ionizer can first be attached to the aerosol(s). A collection surface of the opposite charge can then be used to attract and collect the aerosol(s). Water continuously flowing down the collection surface can wash and carry the biological agents to a reservoir below (not illustrated). Because charging efficiency can be decreased as aerosol size decreases, the amplified aerosol(s) can be more easily charged and subsequently collected.

FIG. 3 shows an example of bubble sample in an impinger fluid 300 in accordance with the principles of the present teachings. It should be readily apparent to those of ordinary skill in the art that the impinger fluid 300 containing amplified bioaerosol(s) shown in FIG. 3 represents a generalized system illustration and that other components can be added or existing components can be removed or modified while still remaining within the spirit and scope of the present teachings. For example, the immersion fluid can be Ringer's solution or phosphate buffer solution to help maintain the viability of the collected biological agents.

In particular, the impinger fluid 300 can include the immersion fluid 310, a bubble sample 320 in the immersion fluid, and survived bioaerosol(s) 340, e.g., biological agents in the immersion fluid. The bubble 320 can further include bioaerosol(s) 330 amplified at various stages and collected in the bubble.

The number of amplified bioaerosols 330 shown in FIG. 3 within the bubble 320 is shown for example purposes only. One of ordinary skill in the art would understand that the number of amplified bioaerosols 330 within a particular bubble 320 in the immersion fluid 310 can be more or less than that shown in FIG. 3.

Referring back to FIG. 1, the bioaerosol detection system 100 disclosed herein can be used for, e.g., sampling bioaerosols for laboratory studies and field characterization related to disease transmission, homeland security, force protection, environmental air sampling, public health sampling, pharmaceutics, drug delivery, etc. In addition, the bioaerosol detection system 100 can be used by many entities, e.g., military units, homeland security units, public health organizations, environmental protection agencies, etc.

In accordance with the teachings disclosed herein any biological agent, e.g., submicron/nano bioaerosol, within the sample volume 110 can be amplified and concentrated to more easily detect and quantify the biological agent therein. Once the biological agent can be concentrated, the teachings disclosed herein apply to any conventional method, e.g., bioassay, fluorescence techniques, polymerase chain reaction (PCR), enzyme-linked ImmunoSorbent assay (ELISA) etc., of detecting, identifying, and quantifying the particular biological agent, e.g., avian flu, protein, or small pox, etc.

FIGS. 4A-4B show an example of a condensational amplification system 400 that includes, e.g., two parallel tubes in which humidification and size amplification occur sequentially in tandem, in accordance with the principles of the present teachings. It should be readily apparent to those of ordinary skill in the art that condensational amplification system 400 shown in FIGS. 4A-4B represents a generalized system illustration and that other components can be added or existing components can be removed or modified while still remaining within the spirit and scope of the present teachings.

As shown in FIG. 4A, the condensational amplification system 400 can include a humidifier (or saturator) 410 including a heating tube 414, a size amplifier 420 including a cooling tube 426, a pump and reservoir 430, and a power supply 440. Sample gas 110 can pass into the humidifier 410 at humidifier entrance 412, exit across into the size amplifier 420 at the amplifier entrance 422, and finally leave the system 400 at an amplifier exit 424.

In various embodiments, temperatures can be monitored at the entrance and exits of both the heating tube 414 and the cooling tube 426, while humidity can be measured at the exits of both tubes. The heating tube 414 and the cooling tube 426 can be, e.g., two parallel aluminum square tubes; and a temperature difference can be produced therebetween. In various embodiments, the length of both the heating and cooling tubes 414 and 426 can be an important factor for the proper operation of the amplification device. In an exemplary embodiment, for an air stream entering the cooling tube at about 40° C. and a surface temperature of about 10° C., the required length to cool the air stream to 25° C. can be approximated to be about 0.92 m (3.01 ft). In various embodiments, the temperature difference can range from about 10° C. to about 45° C. For example, after the air stream (e.g., the sample volume 110) that contains bioaerosols has passed through the heating tube 410, the air stream can have a temperature of, e.g., about 40° C., and then enter into the cooling tube 426. After passing through the cooling tube 426, the air stream can have a cooled temperature of, e.g., about 25° C.

Note that the tube dimensions and material used herein for the system 400 can have a large bearing on the temperature difference produced, but should not be considered as a critical component of the invention, rather a necessary design to meet the required temperature differences.

The temperature difference produced between the two tubes 414 and 426 can be obtained, e.g., by means of heat pumps, such as Peltier thermoelectric heat pumps. For example, the system 100 can include a plurality of Peltier arrays with a number of Peltier junctions distributed between a cooling base 472 and a heating base 474. The two bases 472 and 474, e.g., two aluminum bases, can be attached to the heating and cooling tubes 414 and 426. The bases can be used to evenly distribute the intermittent thermal flux from the heat pumps to the tubes.

FIG. 4B shows a cross sectional detailed view of a condensational amplification system 400 shown in FIG. 4A in accordance with the principles of the present teachings.

In particular, the condensational amplification system 400 is shown to further include an evaporative material 450, a liquid supply channel 460, a Peltier thermoelectric heat pump 470 and an insulation 480.

The Peltier thermoelectric heat pump 470 can remove heat from one tube (e.g., cooling it) and deliver it to the parallel one (e.g., heating it). For example, Peltier thermoelectric heat pumps can be used to heat and cool the exemplary parallel aluminum square tubes respectively by producing a heat flux 477 across two bases 472 and 474, e.g., drawing heat from the cooling tube 426 and delivering it into the heating tube 414. This can allow the bioaerosol detection system 400 to be free from external hot and cold sources and to be more rugged for field use. By varying the amount of voltage and current supplied to the Peltier array(s), the effective tube temperature differences between the hot and cold sections can be controlled so as to produce desired supersaturated conditions.

High relative humidity, e.g., water vapor, can be produced in the heating tube 414 by the evaporative material 450, which can be porous and hydrophilic, and can be wetted by means of the liquid supply channel 460. Exemplary porous evaporative material can include those produced by Porex Inc. The liquid supply channel 460 can be embedded in the base 474 of the heating tube 414 and can supply a flow of water into the evaporative material 450, such as a porous strip, where it then transpires and evaporates into the flowing stream. The exemplary water stream passing through the channel can be part of a closed circuit of water flowing via the small pump and reservoir 430 seen in FIG. 4A. That is, the closed-circuit liquid pump and reservoir 430 can feed the liquid supply channel 460.

In operation, when the bioaerosol sample flow 110 enters the heated tube, bioaerosol(s) can be saturated with water vapor and can pass through the cooled tube, where condensation can occur on the bioaerosol nuclei for their size amplification.

External insulation 480 can cover all exposed surfaces in order to minimize energy transfer to the environment and thus preserve the efficiency and effectiveness of the heating and cooling of the condensational amplification system 400.

In various embodiments, the system 400 can be modified in various manners. For example, the system 400 can further include a secondary set of heat-pumps to the amplification section as shown in FIGS. 5A-5B.

FIGS. 5A-5B depict another example of a condensational amplification system 500 in accordance with the principles of the present teachings. It should be readily apparent to those of ordinary skill in the art that condensational amplification system 500 shown in FIGS. 5A-5B represents a generalized system illustration and that other components can be added or existing components can be removed or modified while still remaining within the spirit and scope of the present teachings.

In various embodiments, the system 500 can include a row of heat pumps with each including, e.g., a Peltier heat pump 570 on a heat base 574 that is installed on the amplification section 420. In various embodiments, the heat pump 570 can be similar to the heat pump 470 as described herein. The heat base 574 can also be a heat sink to draw heat from the cold side (the amplification side 420) of the system.

In this case, the temperature difference between the humidification (see 410) and amplification (see 420) sections can be increased such that a larger amount of condensation can occur on the bioaerosol and thereby result in a larger particle and higher collection efficiency. In addition, the heat pumps assembled on the cold side of the system can be suitable for live media because high (or hot) temperatures can become harmful to the live media. Further, the temperature difference can be continuously controlled via the first set of heat pumps 470 while the relative temperature can be controlled by the second set of heat pumps 570.

In an exemplary embodiment, the system 500 can be used to control a humidification section temperature of about 35° C. or lower and an amplification section temperature of about 16° C. or lower.

Various embodiments can also include any other devices incorporated with the condensational amplification systems 400 and/or 500. For example, a hydration device, such as a nebulizer device, can be incorporated to provide, e.g., a saturated wet air stream, to the sample flow 110 of the system 400/500. When the hydration device is used, the hydrophilic evaporative material 450 can be removed from the system 400 and/or 500. However, one of ordinary skill in the art would understand that the evaporative material 450 can still be used for the condensational amplification system 400/500 of the disclosed bioaerosol detection system.

Figure 6:
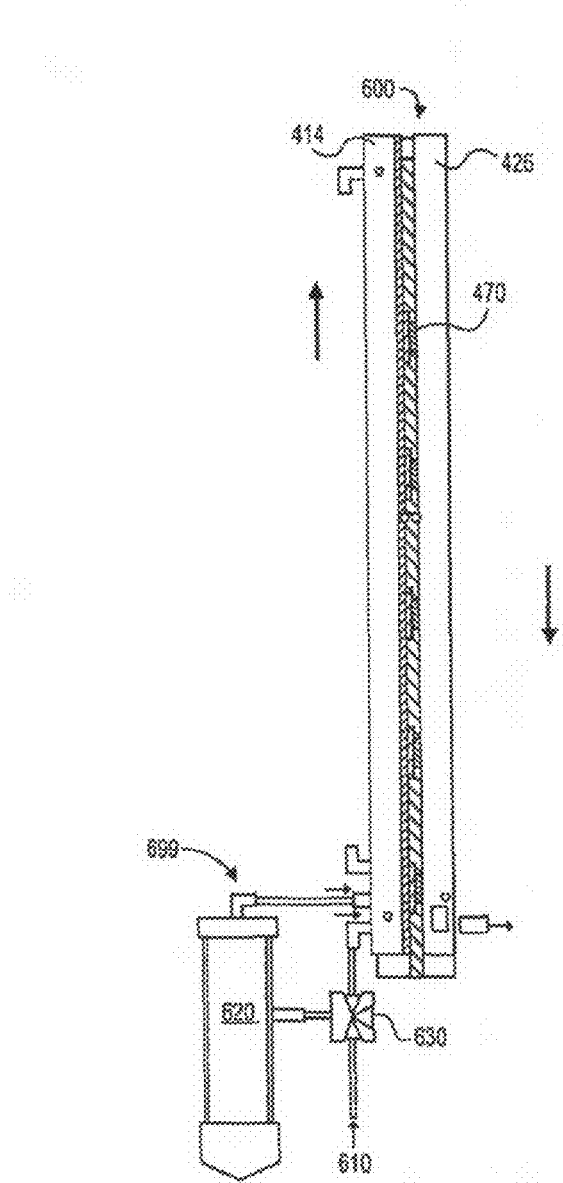
FIG. 6 shows an additional exemplary condensational amplification system for FIG. 1 in accordance with the present teachings.

For example, the hydration device can include an ultrasonic nebulizer device or a pneumatic atomizer and physical integrity of all connections, parts, and structures for eliminating chances of leaks and ensuring pressure capabilities; reduced pressure drop; easy ability to dismantle in case of maintenance; and/or means of inspecting several sections of the device. FIG. 6 depicts an additional exemplary condensational amplification system 600 having a nebulizer device 699 in accordance with the present teachings.

As shown, the system 600 can include the nebulizer device 699 incorporated with the condensational amplification system 400 of FIG. 4 and can include a nebulizer chamber 620 containing, e.g., saturated wet air stream, and a valve 630.

When in operation, the valve 630, e.g., a 3-way valve, can be used to distribute the sample air 610, the majority of which passes directly into the humidification section 410. The remaining air stream fraction can be bypassed into the nebulizer chamber 620, where it dilutes the saturated air mist. The wet air exited from the nebulizer chamber 620 can then be mixed with the sample air from the valve 630 at the humidification tube entrance 414. As described above, RH meters can be located at the beginning and end of the tube 414 to monitor the unit functionality, and the air reflux ratio between the portion of the sample flow through the valve 630 or into the nebulizer chamber 620 can be adjusted in order to control a desirable humidity level. Likewise, as depicted in FIG. 4, at the end of the humidification section, the sample air can be passed over to the amplification tube section 426 via the cross-over tube at 422. The processed sample air can exit the bottom end of the amplification tube 426, where the RH can also be measured.

Figure 7:
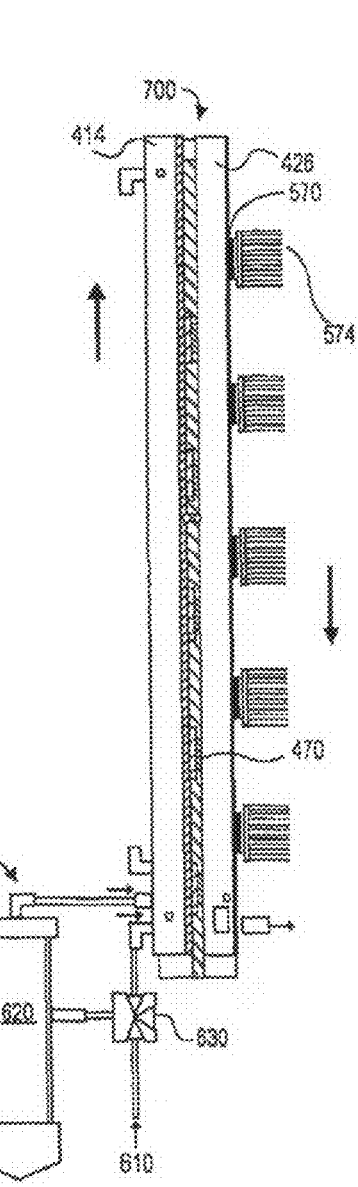
FIG. 7 shows a further exemplary condensational amplification system for FIG. 1 in accordance with the present teachings.

FIG. 7 depicts a further exemplary condensational amplification system 700 having the nebulizer device 699 of FIG. 6 incorporated into the system 500 of FIGS. 5A-5B in accordance with the present teachings. Compared with the system 600 of FIG. 6, the system 700 can include a row of heat pumps installed on the amplification section 420, with each heat pump including, e.g., a Peltier heat pump 570 on a heat base 574 as that described in FIG. 5. The heat base 574 can be a heat sink to draw heat from the cold side (the amplification side 420) of the system. The temperature difference between the humidification (see 410) and amplification (see 420) sections can therefore be further controlled such that a larger amount of condensation can occur on the labile aerosol and thereby resulting in a larger particle and higher collection efficiency.

EXAMPLE

Detection and Sampling of MS2 Type Bacteria

A bioaerosol generation system was connected to an assembled bioaerosol detection system (e.g., see FIG. 1 and FIGS. 4A-4B) having Six 8 W Peltier junctions for an inline analysis of capture efficiency. MS2 type bacteria phages were chosen as the test sample because of their representative size for the most challenging viral aerosols (28 nm). Baseline tests were performed with the aerosol detection device connected but being turned off in order to obtain an accurate account for the effects of the aerosol size amplification. Humidity at the exit of the heating tube was measured to ensure an ultimate humidity of at least 90% (relative). Four temperatures at the beginning and ends of both the tubes were measured.

Results from the experiments were collected and are displayed in Table 1. As shown in Experiment I, for the baseline (see set 1 or 5) with the size amplification system turned off, the concentration of MS2 was on average of about 78000 PFU; however, with the size amplification system turned on (see sets 2-4), the concentration was nearly doubled to an average of about 146000 PFU over three consecutive samples. This trend was repeated in Experiment II of Table 1. As compared with sets 6 and 9, the sets 7 and 8 show the recovery fraction was also nearly doubled once the size amplification device was activated.

TABLE 1

|  | Set | Sampling Time (30 min) | $T_H$ (°C.) | $T_C$ (°C.) | Amplification Condition | Concentration (PFU) | Time-Mean Concentration (PFU) |
|---|---|---|---|---|---|---|---|
| Experiment I | 1 | Control | 27 | 27 | Off ΔT = 0° C. | 76000 | 78000 |
|  | 5 | Control | 24 | 24 | Off ΔT = 0° C. | 80000 |  |
|  | 2 | Experiment | 39 | 19 | ΔT = 20° C. | 166000 | 146000 |
|  | 3 | Experiment | 43 | 21 | ΔT = 20° C. | 131000 |  |
|  | 4 | Experiment | 43 | 23 | ΔT = 20° C. | 143000 |  |
| Experiment II | 6 | Control | 27 | 27 | Off ΔT = 0° C. | 41000 | 39250 |
|  | 9 | Control | 24 | 24 | Off ΔT = 0° C. | 37500 |  |
|  | 7 | Experiment | 39 | 19 | ΔT = 20° C. | 52000 | 70500 |
|  | 8 | Experiment | 43 | 21 | ΔT = 20° C. | 89000 |  |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A bioaerosol collection system comprising:
a humidifier to increase the humidity of a continuously flowing sample volume using a biocompatible liquid vapor for humidification, wherein the continuously flowing sample volume comprises one or more bioaerosols in a gas stream; and
an amplifier to condense vapor of the biocompatible liquid on the one or more bioaerosols of the continuously flowing sample volume from the humidifier, thereby amplifying particle sizes of the one or more bioaerosols,
wherein humidification is performed in a heating tube within the humidifier and amplification is subsequently performed in a cooling tube within the amplifier; and the heating tube and cooling tube are positioned to be parallel to each other such that the continuously flowing sample volume enters the amplifier after exiting the humidifier.

2. The system of claim 1, further comprising one or more of a biocompatible impinger, a biocompatible impactor, a biocompatible cyclone separator, a biocompatible electrostatic precipitator and a biomass spectroscopy system connected to the amplifier.

3. The system of claim 2, further comprising a vacuum adaptively attached to the one or more of the biocompatible impinger, the biocompatible impactor, the biocompatible cyclone separator, the biocompatible electrostatic precipitator and the biomass spectroscopy system.

4. The system of claim 2, wherein the biocompatible impactor is one of a single stage impactor or a multi-stage impactor.

5. The system of claim 1, wherein the one or more bioaerosols have a particle size of about 10 nm to about 300 nm in diameter before amplification.

6. The system of claim 1, wherein each of the one or more bioaerosols comprises virus, bacteria or protein.

7. The system of claim 1, wherein the humidifier increases the humidity to a relative humidity of about 90% or higher.

8. The system of claim 1, further comprising a temperature difference between the heating tube and the cooling tube, wherein the temperature difference ranges from about 10° C. to about 45° C.

9. the system of claim 1, further comprising a plurality of heat pumps to produce a heat flux from the cooling tube to the heating tube.

10. The system of claim 9, further comprising a secondary set of heat-pumps connected to the amplifier to further control the temperature difference between the cooling tube and the heating tube.

11. The system of claim 1, further comprising one or more of a nebulizer device and an evaporative material incorporated with the humidifier to control the humidity of the continuously flowing sample volume.

12. A method of collecting a bioaerosol comprising:
increasing a humidity of a continuously flowing sample volume containing one or more bioaerosols; and
amplifying the humidified one or more bioaerosols by condensing vapor thereon,
wherein the method uses the system of claim 1.

13. The method of claim 12, further comprising collecting the amplified bioaerosols by impaction, impingement, centrifugal separation or electrostatic attraction.

14. The method of claim 13, further comprising forming a bubble sample in an immersion fluid of the impingement, wherein the bubble sample comprises the amplified one or more bioaerosols.

15. The method of claim 12, further comprising characterizing the amplified bioaerosols by a biomass spectroscopy, 16. The method of claim 12, further comprising pulling the bioaerosols with a vacuum.

17. The method of claim 12, wherein the vapor condensation further protects the bioaerosols from environmental stress and maintains viability thereof.

18. The method of claim 12, further comprising effectively amplifying each of the bioaerosols from an ultrafine particle to a supermicron droplet by the vapor condensation.

19. The method of claim 12, further comprising determining the length of the heating tube for humidity increasing or the cooling tube for the vapor condensing by a temperature difference between the heating tube and the cooling tube.

20. A bioaerosol detection system comprising:
a humidifier comprising a heating tube to increase the humidity of a continuously flowing sample volume using a biocompatible liquid vapor for humidification, wherein the continuously flowing sample volume comprises one or more bioaerosols in a gas stream;
a nebulizer device connected to the humidifier to further control the humidity of the continuously flowing sample volume;
an amplifier comprising a cooling tube to condense vapor of the biocompatible liquid on the one or more bioaerosols of the continuously flowing sample volume from the humidifier, thereby amplifying particle size of the one or more bioaerosols;

a plurality of heat pumps disposed between the humidifier and the amplifier to provide a temperature difference between the humidifier and the amplifier;

a secondary set of heat pumps connected to the amplifier to further control the temperature difference between the humidifier and the amplifier; and one or more of a biocompatible impinge, a biocompatible impactor, a biocompatible cyclone separator, a biocompatible electrostatic precipitator and a biomass spectroscopy system to collect the amplified bioaerosols, wherein the heating tube and cooling tube are positioned to be parallel to each other such that the continuously flowing sample volume enters the amplifier after exiting the humidifier.

* * * * *